(12) United States Patent
Goyal

(10) Patent No.: US 10,932,802 B2
(45) Date of Patent: Mar. 2, 2021

(54) THROMBUS RETRIEVAL STENTS AND METHODS OF USING FOR TREATMENT OF ISCHEMIC STROKE

(71) Applicant: Mayank Goyal, Calgary (CA)

(72) Inventor: Mayank Goyal, Calgary (CA)

(73) Assignee: MG Stroke Analytics Inc., Calgary (CA)

(*) Notice: Subject to any disclaimer, the term of this patent is extended or adjusted under 35 U.S.C. 154(b) by 91 days.

(21) Appl. No.: 16/071,103

(22) PCT Filed: Jan. 24, 2018

(86) PCT No.: PCT/CA2018/050082
§ 371 (c)(1),
(2) Date: Jul. 19, 2018

(87) PCT Pub. No.: WO2018/137029
PCT Pub. Date: Aug. 2, 2018

(65) Prior Publication Data
US 2019/0336147 A1   Nov. 7, 2019

Related U.S. Application Data

(60) Provisional application No. 62/450,835, filed on Jan. 26, 2017.

(51) Int. Cl.
*A61B 17/221* (2006.01)

(52) U.S. Cl.
CPC .... *A61B 17/221* (2013.01); *A61B 2017/2212* (2013.01)

(58) Field of Classification Search
CPC .... A61B 2017/2212; A61B 2017/2215; A61B 2017/2217; A61B 17/22; A61B 17/221; A61F 2/01; A61F 2/011; A61F 2/012
See application file for complete search history.

(56) References Cited

U.S. PATENT DOCUMENTS

| | | | |
|---|---|---|---|
| 9,339,331 B2 | 5/2016 | Tegg et al. | |
| 9,642,635 B2 | 5/2017 | Vale et al. | |
| 2011/0054504 A1* | 3/2011 | Porter | A61M 29/02 606/159 |
| 2011/0213403 A1* | 9/2011 | Aboytes | A61F 2/013 606/194 |
| 2012/0016407 A1* | 1/2012 | Sakai | A61B 17/320725 606/200 |
| 2013/0053882 A1* | 2/2013 | Hocking | A61B 17/221 606/200 |

(Continued)

*Primary Examiner* — Martin T Ton
(74) *Attorney, Agent, or Firm* — McGlew and Tuttle, P.C.

(57) ABSTRACT

Methods and apparatus for retrieving a blood clot are disclosed. The apparatus comprises an expandable wire frame for deployment using a push wire within a microcatheter. When deployed in the vicinity of a blood clot, the wire frame is configured to expand and trap the blood clot allowing the blood clot to be removed. The expandable wire frame is connected to the push wire at distal and proximal ends. One or more expansion stops define a minimum distance between the distal and proximal ends of the expandable wire frame and a point of maximum extension of the expandable wire frame. This may help the user to control the configuration of the apparatus as it is being used within the vascular system.

17 Claims, 8 Drawing Sheets

(56) References Cited

U.S. PATENT DOCUMENTS

2014/0200648 A1\* 7/2014 Newell ................... A61F 2/844
                                                              623/1.11
2015/0182361 A1    7/2015 Ferrera et al.

\* cited by examiner

THROMBUS RETRIEVAL STENTS AND METHODS OF USING FOR TREATMENT OF ISCHEMIC STROKE

FIELD OF THE INVENTION

The invention relates to systems and methods for retrieving blood clots (thrombi) from patients undergoing endovascular/neurointervention procedures following ischemic stroke. More specifically, clot retrieval devices effective in ensnaring thrombi and preventing collapse of the clot retrieval device during withdrawal are described as well as methods of utilizing these devices.

BACKGROUND OF THE INVENTION

The human body has an extensive network of blood vessels including both the venous and arterial systems for circulating blood throughout the body. The occurrence and/or development of restrictions to flow within the circulatory system can result in serious medical conditions, the most significant being myocardial infarction and ischemic stroke. The treatment of both conditions (and others involving the circulatory system) continues to evolve with many new techniques and equipment being utilized to effect treatment.

In recent years, a variety of traumatic surgical procedures have been replaced with procedures that involve the use of one or more catheters being advanced through the vascular system of the body to gain access to diagnose and/or treat issues involving the vasculature of a particular organ. For example, ischemic strokes caused by blood clot blockages in the brain, coronary artery blockages within the heart and various heart defects may be treated by advancing catheters to the affected site whence various procedures can be initiated to treat the problem. Stents having various structural and functional properties can be positioned and deployed at a location where intervention is required wherein the specific structure of the stent can allow the treatment of a medical problem. Catheter procedures are also undertaken in other parts of the body including the leg vessels and renal arteries and other complex percutaneous procedures including treatment of valvular heart disease, aortic dissections, dysrhythmias, and management of shunts for dialysis patients can also be performed using catheter systems. Further, complex aneurysms in the brain and other locations are increasingly being treated through a percutaneous endovascular route.

It is known that when a patient experiences a significant ischemic stroke event, those portions of the brain distal to the occlusion that experience a dramatic reduction in blood supply will affect the functioning of large regions of neurons. This reduction in blood supply may cause the patient to become symptomatic, cause the death of regions of the brain and/or put regions of the brain at the risk of dying if not treated quickly. Depending on the location and size of the occlusion will result in a wide range of symptoms in the patient and depending on the severity will ultimately determine how a physician may choose to intervene or not.

Time delays in effecting treatment will typically result in the death of a greater number of neurons. Table 1 shows that in the specific case of acute ischemic stroke, the pace or rate of neural circuitry loss in a typical large vessel supratentorial acute ischemic stroke can be very rapid.

TABLE 1

Estimated Pace of Neural Circuitry Loss in Typical Large Vessel, Supratentorial Acute Ischemic Stroke

| | Neurons Lost | Synapses Lost | Myelinated Fibers Lost | Accelerated Aging |
|---|---|---|---|---|
| Per Stroke | 1.2 billion | 8.3 trillion | 7140 km/ 4470 miles | 36 yrs |
| Per Hour | 120 billion | 830 billion | 714 km/ 447 miles | 3.6 yrs |
| Per Minute | 1.9 million | 14 billion | 12 km/ 7.5 miles | 3.1 weeks |
| Per Second | 32,000 | 230 million | 200 meters/ 218 yards | 8.7 hours |

The numbers presented above represent an average with it also being known that there is a high degree of variability in the above numbers generally depending on the available blood supply to the ischemic region through collateral channels. However, and importantly, delays in making a decision in the order of only a few minutes can have a significant impact on neural circuitry loss and ultimately patient outcome. Further, even slight variations in blood supply can tip the balance and dramatically further increase the rate of cell death if blood supply is reduced or, alternatively prevent neural cell death if blood supply is restored quickly.

The recent paper "Analysis of Workflow and Time to Treatment and the Effects on Outcome in Endovascular Treatment of Acute Ischemic Stroke: Results from the SWIFT PRIME Randomized Controlled Trial" (M. Goyal et al., Radiology, (2016), 279 (3): 888-97, doi: 10.1148/radiol.2016160204), and incorporated herein by reference, quantitatively shows that there is a definitive improvement in patient outcome through fast reperfusion. In particular, this study concluded that "aggressive time goals may have contributed to efficient workflow environments". Further, the study quantifies inter alia that functional independence of a patient was significantly higher when treated quickly (i.e. within 2.5 hours of stroke onset).

Importantly, it is now known that efficient workflows during a recanalization procedure (of which the effectiveness of a stent is important) provide better outcomes.

In diagnosing and treating ischemic stroke, it is important for the physician to know where the vessel occlusion is, how big the occlusion is, where any dead brain tissue (termed "core") is and, how big and where is the brain tissue that may have been affected by the ischemic event but that may potentially be saved (termed "penumbra").

The penumbra is tissue around the ischemic event that can potentially stay alive for a number of hours after the event by the perfusion of this tissue by collateral arteries. The collateral arteries may provide sufficient oxygen, nutrients and/or flushing to the penumbra tissue to prevent this tissue from dying for a period of time.

When responding to acute ischemic stroke, endovascular treatment of acute ischemic stroke due to large vessel occlusion in the anterior circulation is now the standard of care for patients under certain criteria. That is, patients exhibiting particular symptoms (i.e. stroke symptoms of a particular severity) will benefit from early and rapid endovascular intervention to open occluded blood vessels. During various endovascular treatments, a surgeon will advance clot-retrieval and/or clot-suction devices into the brain's vasculature to the location of the clot where the clot is either withdrawn and/or aspirated from the clot site.

There are many anatomical and situational considerations that can affect the severity and ultimately treatment of ischemic stroke. Importantly, as described above, while a blood clot may severely affect blood flow to the ischemic area, some blood flow may get to the ischemic area if collateral arteries are functioning to at least partially perfuse the affected area.

The most common large vessel occlusion that is treated by endovascular techniques is the M1 segment of the middle cerebral artery (MCA). When a patient has an M1 occlusion, the territory supplied by the M1 receives a dramatic reduction in blood supply. As a consequence distal neurons don't function well and the patient becomes symptomatic. Preferably, there is some blood flow that manages to get to the ischemic territory through collaterals which may decrease the rate of neuronal death. Generally, in this case, the collaterals are the connections between the distal most branches of the anterior cerebral artery and the middle cerebral artery (or the posterior cerebral artery and the middle cerebral artery).

In different patients, collaterals are highly variable and there are a number of factors at play which are not fully understood. Some of these factors are genetic in nature but conditions such as hypertension and diabetes (and other poorly understood factors) may also reduce the efficacy of collaterals in different patients.

Regardless of the patient's anatomy, the maintenance of collateral blood flow is critical to keep the brain alive until the time the occluded vessel can be recanalized and blood flow re-established.

Recanalization procedures utilize a wide range of equipment and techniques to access a clot and effect its removal. Generally, the endovascular surgeon will have a number of tools at their disposal including a wide range of guide catheters, microcatheters, microwires, stents and other tools that individually have properties, features and functions that are effective for different procedures and patient presentations.

When an endovascular surgeon deploys a stent to retrieve a clot, the stent is generally conveyed to the clot within a microcatheter in a compressed state. The typical modern stent is a fine mesh of wires that once expanded form a small network of criss-crossing wires that upon deployment penetrate the surface of the clot and otherwise engage with the clot to allow the clot to be drawn proximally from the occlusion site and removed from the body. Generally, engagement of the wires with the clot requires that the wires penetrate the surface of the clot in a manner that sufficient friction and/or interfacial forces between the clot and wires exist to wholly and fully allow the clot to be withdrawn. Generally, the mesh of wires can be open or closed cell designs. Generally, most closed cell design stents will foreshorten as they are deployed.

Moreover, when withdrawing the stent, the stent will be subject to various turns and twists within the vasculature as it withdrawn from the occlusion site. For example, the tortuosity of the vessels can cause the stent to collapse as it passes through a curve. As a result, the central axis of the stent will not be continuously aligned with the central axis of the vessel as it is being withdrawn. Thus, the outer wires of the stent do not inherently protect the central axis of the stent. Thus, as it is being withdrawn particularly when it is being drawn around a tight corner which can result in the stent losing or releasing the clot as the wires of the stent may open.

It is also known that the degree of tortuosity within blood vessels increases with age due to multiple factors including atherosclerotic disease, loss of height of the spine, etc. With an aging population and improving technologies, more and more of these procedures are being done in older patients necessitating access despite the increased complexity of conducting procedures through tortuous vessels. As a result, there is a need for improved stents that are more capable of travelling through tighter curves and that are less likely to drop a clot as the clot is being withdrawn. Further still, in these situations, there is a need for an operator to be able to control the relative stiffness of a stent so as to move the stent around a corner while minimizing compression and/or opening of the stent that can cause the clot to become dislodged from the stent.

Accordingly, there has been a need for systems and methods that are more effective in the capture and removal of clots that have advantages over existing retrieval systems. In particular, there has been a need for retrieval systems having effective surfaces and control systems that enable capture of clots and that enable an operator to control the expansion and stiffness of the stent as it is being withdrawn.

SUMMARY OF THE INVENTION

In accordance with the invention, there is provided systems and methods for improving the efficiency of surgical procedures using catheter systems to move from an entry point to a location in the body where a treatment or diagnostic procedure may be completed.

Methods and apparatus for retrieving a blood clot are disclosed. The apparatus comprises an expandable wire frame for deployment using a push wire within a microcatheter. When deployed in the vicinity of a blood clot, the wire frame is configured to expand and trap the blood clot allowing the blood clot to be removed. The expandable wire frame is connected to the push wire at distal and proximal ends. One or more expansion stops define a minimum distance between the distal and proximal ends of the expandable wire frame and a point of maximum extension of the expandable wire frame. This may help the user to control the configuration of the apparatus as it is being used within the vascular system.

According to a first aspect, there is provided a blood clot retrieving apparatus for deployment into a patient's vasculature from a catheter and for retrieving an intravascular blood clot from within the patient's vasculature comprising: a push wire; an expandable wire frame operatively connected to the push wire adjacent a distal end of the push wire, the expandable wire frame having a plurality of expandable wires having distal and proximal ends operatively connected to the push wire, the expandable wire frame expandable from a compressed position within the catheter to an uncompressed deployed position; and, at least one expansion stop positioned on the push wire to define a minimum distance between the distal and proximal ends of the expandable wire frame and a point of maximum extension of the expandable wire frame.

Expansion in this context may be considered radial expansion. That is, as the wire frame expands radially its length may shorten. The apparatus may be configured such that the radially expanded diameter of the wire frame is less than the length of the wire frame.

One or more of the expansion stops may be fixed with respect with the push wire.

Each expandable wire may define a generally arcuate shape (e.g. in a partially or fully expanded position) between a distal end fixed to the push wire and a proximal end slidingly engaged with the push wire.

The expansion stop may be an enlarged section fixed to the push wire. For example, the expansion stop may be a portion of the push wire with a larger diameter.

The expandable wire frame may comprise one, two or more helical wires extending between the proximal and distal ends of the expandable wire frame.

The expandable wire frame may comprise at least two helical wires extending between the proximal and distal ends of the expandable wire frame and wherein the at least helical wires intersect over one another.

Two or more expandable wire frames may be operatively connected to the push wire and the distal end of each expandable wire frame is fixed to the push wire.

Two or more expandable wire frames may be operatively connected to the push wire.

Two or more expandable wire frames may be operatively connected to the push wire and the distal end of the distal expandable wire frame is fixed to the push wire and each proximally expandable wire frame(s) are slidingly engaged with the push wire.

The apparatus may include a proximal microcatheter stop frictionally engaged with the push wire for engagement with a proximal end of the proximal most expandable wire frame.

The apparatus may include a proximal microcatheter plug slidingly engaged with the push wire for engagement with a proximal end of the proximal most expandable wire frame.

The plug is configured to allow egress from the microcatheter lumen and to restrict entry into the microcatheter lumen once ejected. For example, the plug may be tapered at the distal end and blunted or flared at the proximal end to promote interaction with the microcatheter lumen once ejected. The plug may be configured to expand when deployed from the microcatheter lumen.

In another aspect, the invention provides a method of retrieving a blood clot the method comprising: expanding an expandable wire frame operatively connected to a push wire to trap the blood clot, wherein the expandable wire frame has a plurality of expandable wires having first and second ends operatively connected to the push wire; and, applying a force to at least one of the first and second ends to control the axial length of the expandable wire frame to thereby control the stiffness of the expanded wire frame.

The force may be applied by moving the microcatheter with respect to the push wire, wherein the microcatheter is configured to apply a force to one of the ends via a microcatheter plug.

BRIEF DESCRIPTION OF THE DRAWINGS

Various objects, features and advantages of the invention will be apparent from the following description of particular embodiments of the invention, as illustrated in the accompanying drawings. The drawings are not necessarily to scale, emphasis instead being placed upon illustrating the principles of various embodiments of the invention; however, the scale of the drawings may be relied upon for supporting the relative position of described components with respect to one another. Similar reference numerals indicate similar components.

DETAILED DESCRIPTION OF THE INVENTION

Introduction

With reference to the figures, systems and methods for retrieving blood clots via endovascular intervention are described. More specifically, systems adapted for retaining clots for removal from a patient's vasculature following ischemic stroke are described.

Figure 1:
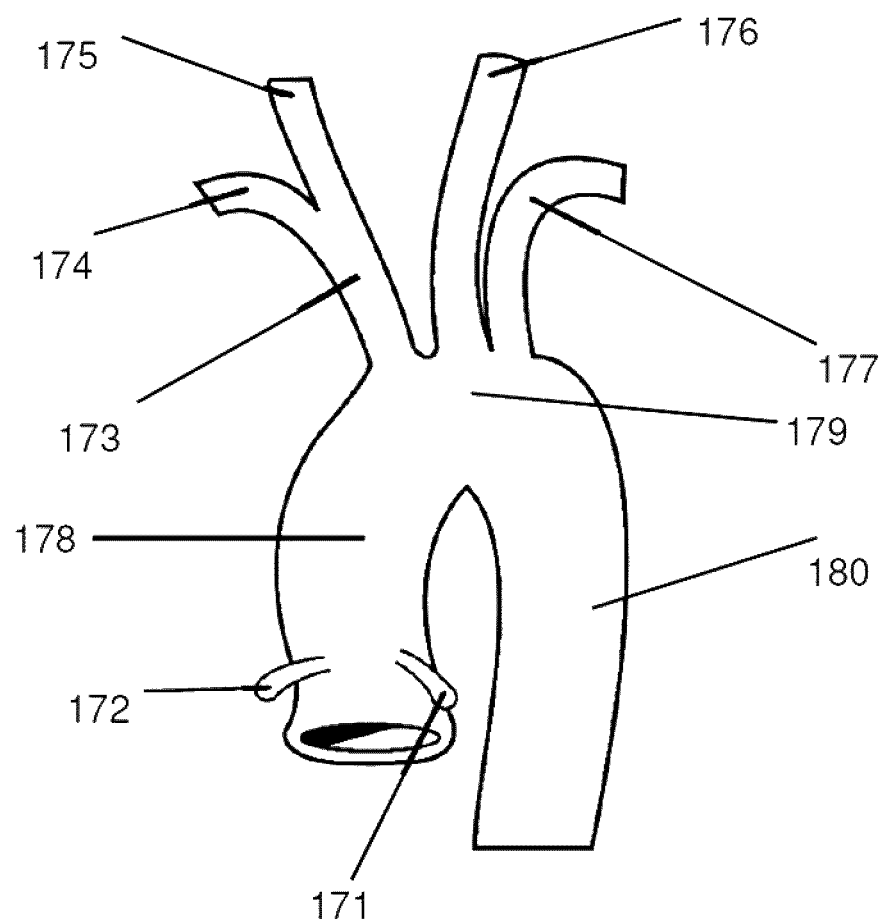
FIG. 1 is a schematic view of an aortic arch and associated blood vessels.

By way of background, FIG. 1 shows a typical aortic arch 179 and various connecting vessels in a human. The aortic arch 179 is connected to the ascending aorta 178 and the descending aorta 180. The ascending aorta is connected to the right and left coronary arteries 171, 172. The aortic arch is connected to the brachiocephalic artery 173 which splits into the right subclavian artery 174 and the right common carotid artery 175. Also connected to the aortic arch are the left common carotid artery 176 and the left subclavian artery.

In a typical endovascular procedure utilizing one or more catheters to access the blood vessels in the head, the interventionist/surgeon typically navigates a catheter system up the descending aorta 180 from the femoral artery and into the aortic arch 179 and into the left common carotid artery 176. For the purposes of the description herein a "catheter system" implies various combinations of an inner guide wire (or microwire), outer catheter (or microcatheter), a distal access catheter (or a balloon guide catheter) and clot retrieval systems that may be advanced to the site of a clot. The various catheters are typically coaxial and can slide over or within the other although non-coaxial systems may also be used. In most procedures, the various components will be selectively moved through the patient's vasculature to a) gain access to the occlusion site and b) deploy a clot retrieval device to remove the clot.

Access to the clot (i.e. via antegrade or distal movement in direction of blood flow) is generally conducted by a combination of advancing a guide wire and advancing a microcatheter over the guide wire through the vasculature by twisting and turning the microcatheter and guide wire in order to direct the distal end of the guide wire and microcatheter into the appropriate vessel.

Clot retrieval devices are typically deployed through a microcatheter after a guide wire has been withdrawn.

Various procedures may also involve a tri-axial approach where the procedure includes advancing an outer catheter (e.g. a 'distal access catheter', 'guide-catheter' or 'balloon guide catheter)' to a position close to the clot and where the outer catheter is used after placement to rapidly advance a microcatheter and/or clot retrieval device to the occlusion site.

In general, it is known that the progression and movement of the various catheters through a patient's vasculature may be varied with the surgeon choosing or utilizing various techniques to advance these tools into a specific and desired location.

For the purposes of general description of the subject invention, it is assumed that the surgeon has advanced a larger guide catheter close to but proximal to the clot and a microwire and microcatheter at or beyond a clot. The microwire has been withdrawn allowing the surgeon to then advance a stent or clot retrieval device through the microcatheter and/or guide catheter where it is pushed out of the end of the microcatheter at or beyond the occlusion. As the stent moves beyond the end of the microcatheter, it expands outwardly and against the walls of the vessel. The surgeon may then simultaneously start to withdraw the microcatheter and stent where the expanded wires of the stent interact with the clot and entrap the clot within the wire cage of the stent. After a short period of time, if the clot has successfully engaged with the wire cage, the microcatheter and stent can be withdrawn into the guide catheter and then withdrawn from the body together with the clot.

Figure 1A:
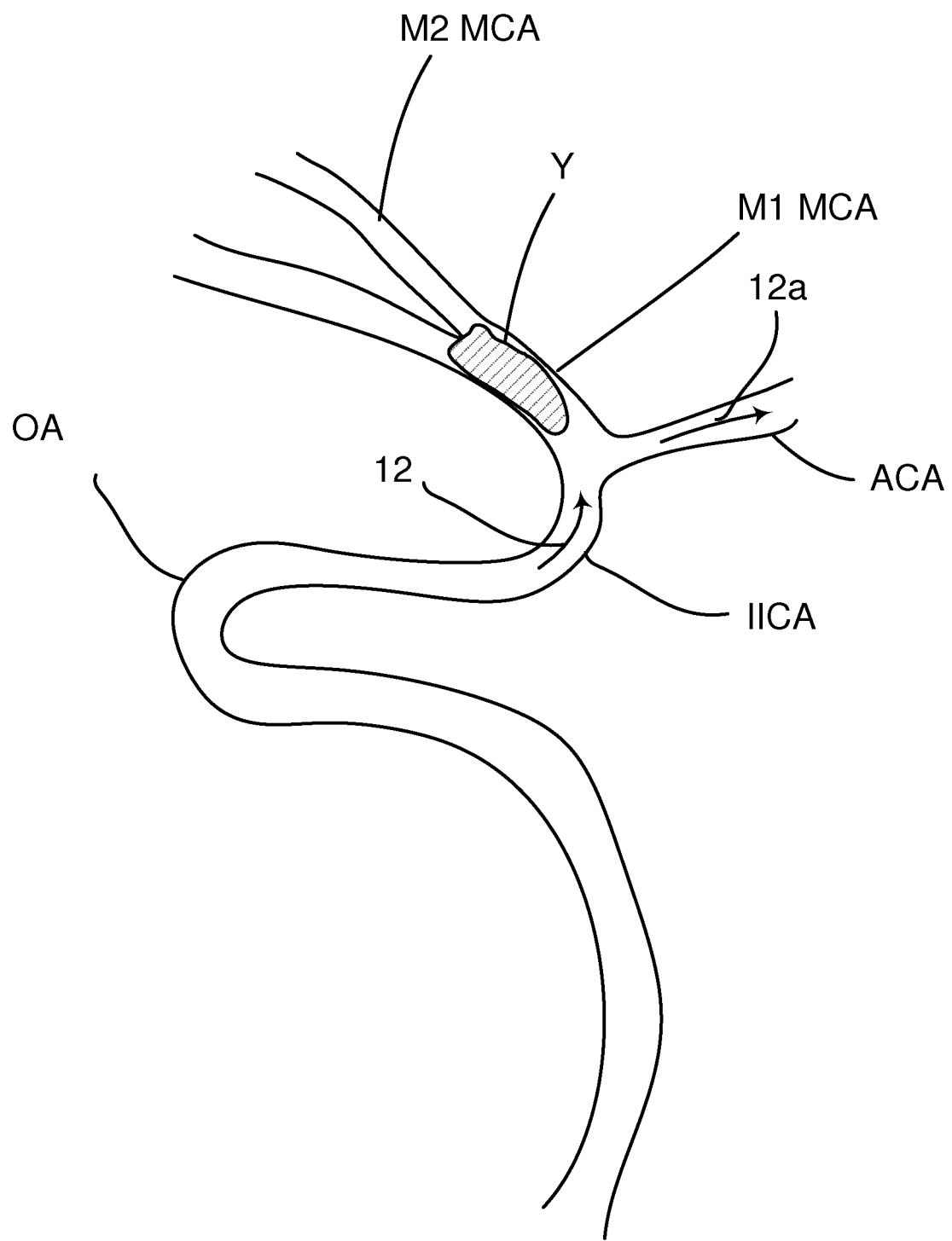
FIG. 1A is a schematic sketch of a portion of brain vascular anatomy showing the ophthalmic artery (OA), intracranial internal carotid artery (IICA), anterior cerebral artery (ACA), M1 segment of the middle cerebral artery and M2 segment of the middle cerebral artery.
Figure 1B:
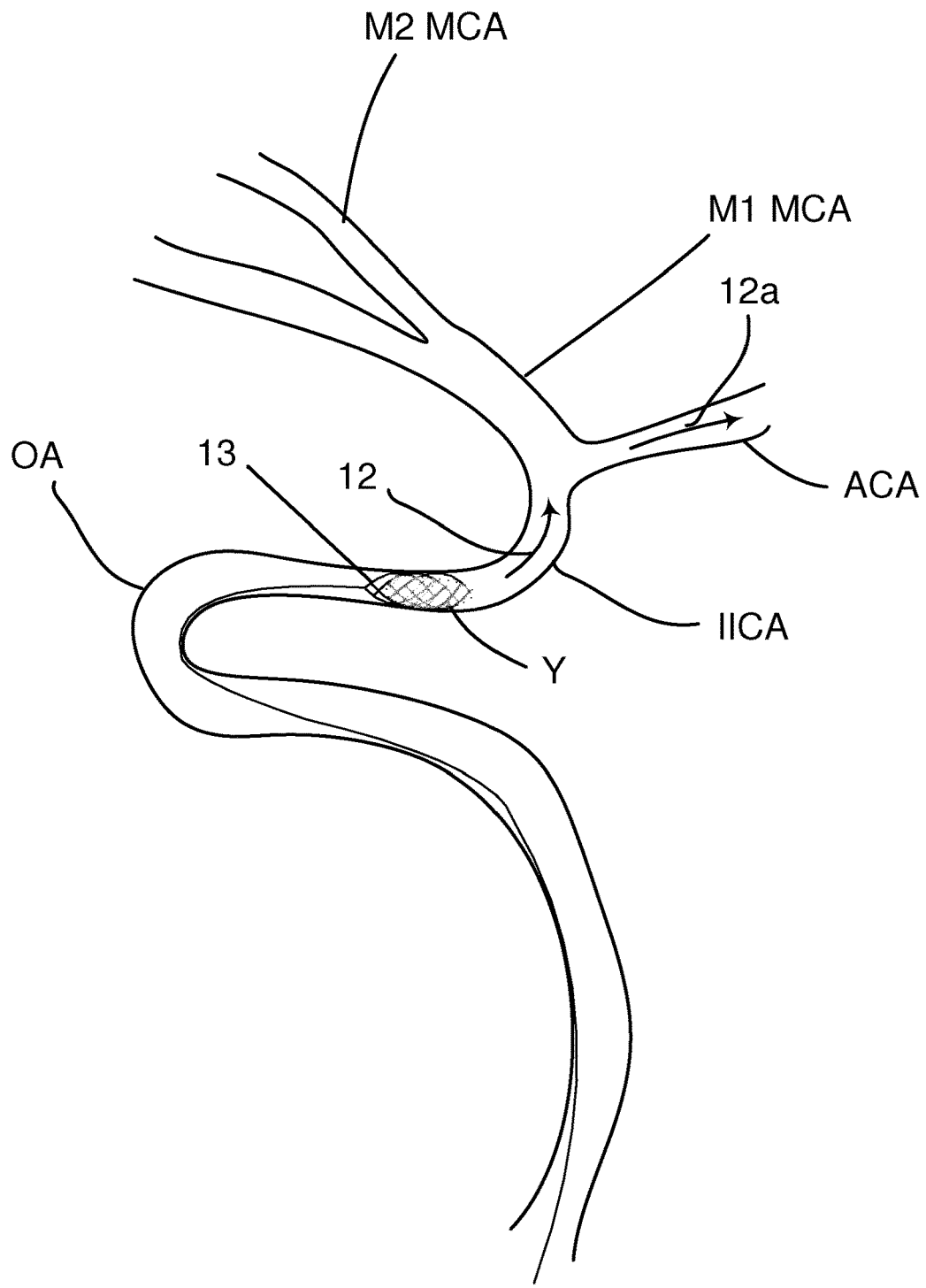
FIG. 1B is a schematic sketch as in FIG. 1A showing a clot retrieval device engaged with a clot during a clot removal procedure.
Figure 1C:
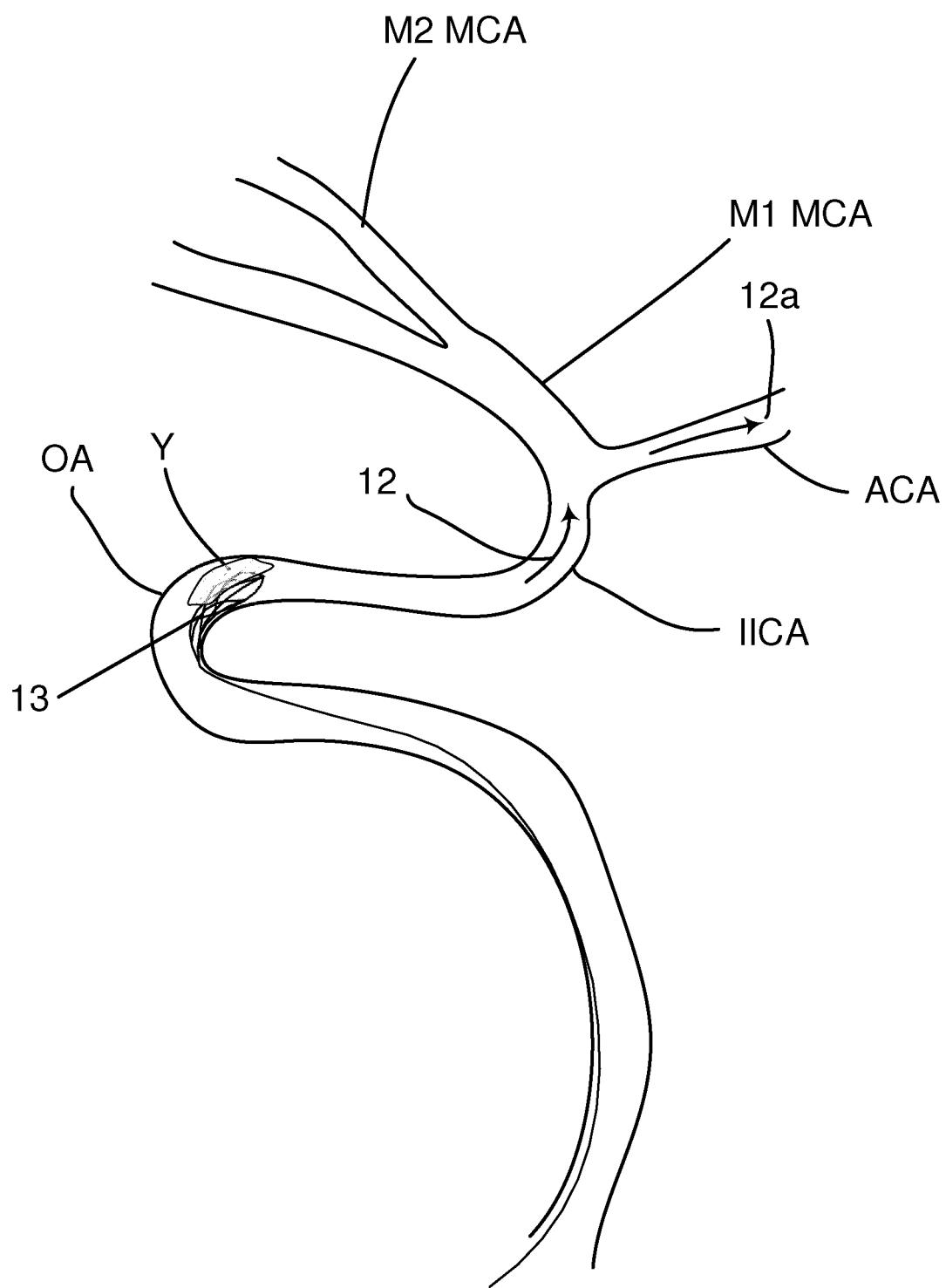
FIG. 1C is a schematic sketch as in FIG. 1A showing a clot retrieval device engaged with a clot during a clot removal procedure and showing how a clot retrieval may compress around tortuous curves. The clot is shown disengaging from the clot retrieval device.

FIG. 1A is a schematic diagram of brain vascular anatomy showing the intracranial internal carotid artery (IICA), anterior cerebral artery (ACA), M1 segment of the middle cerebral artery (MCA) and M2 segment of the middle cerebral artery. A clot Y is shown within the M1 MCA with arrow 12 showing the direction of blood flow prior to any procedure. For the purposes of discussion, it is understood that blood flow 12a through the ACA is supporting collateral perfusion to affected areas of the brain. FIG. 1A also shows a tortuous region (e.g. the ophthalmic artery (OA)) which is a region that can be difficult both to advance and withdraw catheter systems through. In some cases, due to the tortuosity of these vessels, as a surgeon is withdrawing a stent 13 that has been entangled with clot Y (FIG. 1B), the stent 13 may be flattened as it is drawn through a tortuous section resulting in the release or dropping of the clot Y (FIG. 1C) as the wires of the stent move with respect to one another.

Embodiments

Various aspects of the invention will now be described with reference to the figures. For the purposes of illustration, components depicted in the figures are not necessarily drawn to scale. Instead, emphasis is placed on highlighting the various contributions of the components to the functionality of various aspects of the invention. A number of possible alternative features are introduced during the course of this description. It is to be understood that, according to the knowledge and judgment of persons skilled in the art, such alternative features may be substituted in various combinations to arrive at different embodiments of the present invention.

Figure 2:
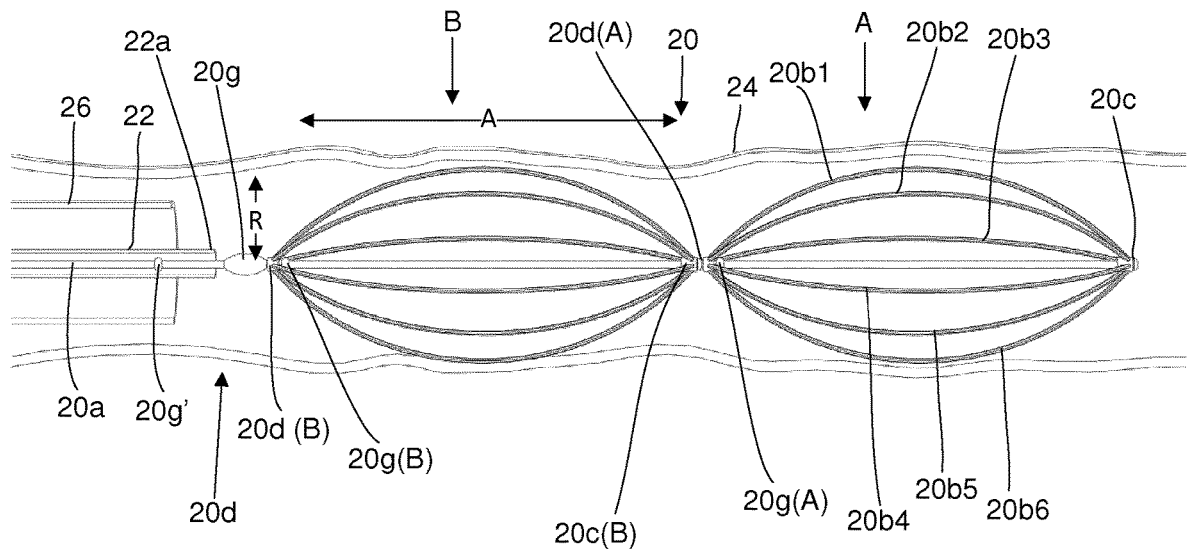
FIG. 2 is a side view of a stent system (clot retrieval system-CRS) in accordance with one embodiment of the invention.
Figure 3:
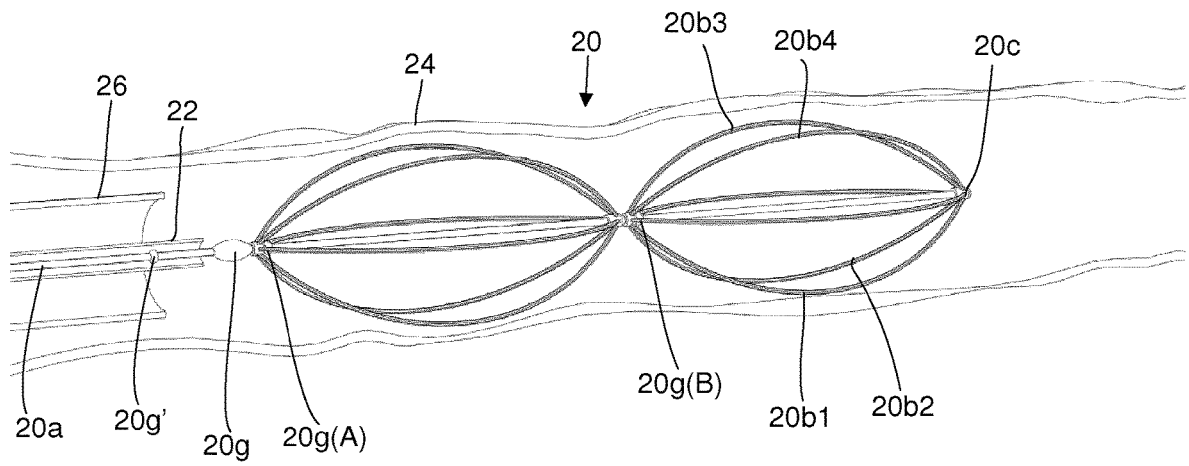
FIG. 3 is a perspective view of a stent system in accordance with one embodiment of the invention.
Figure 4:
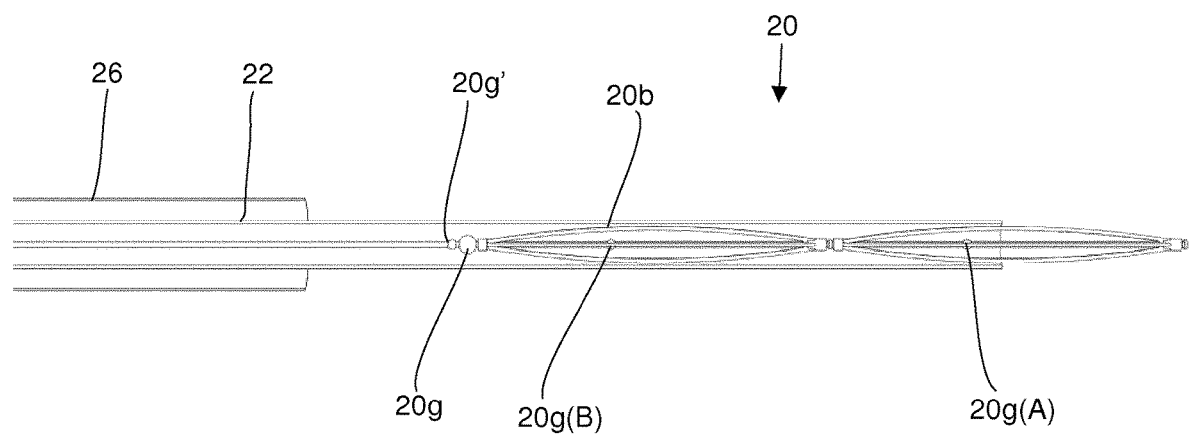
FIG. 4 is a side view of a compressed stent system within a microcatheter in accordance with one embodiment of the invention.

As shown in FIGS. 2-4 and in accordance with one embodiment of the invention, a clot retrieval system (CRS) 20 (also referred to herein as a stent) may be advanced to a position within or beyond a clot within a microcatheter (MC) 22 and within a vessel 24. FIGS. 2 and 3 are a side and perspective view respectively of an expanded CRS 20 within a vessel 24 following deployment from the distal end of a MC. For the purposes of clarity, the CRS is not shown entangled with a clot; although it is generally understood that as the stent is deployed it will be expanding into the clot. Also, for the purposes of illustration a guide catheter 26 (or distal access catheter (DAC)) is also shown adjacent the CRS although in practice it would likely be advanced to a more proximal position relative to the clot. FIG. 4 shows a collapsed CRS as it is being unsheathed from a microcatheter 22.

As best shown in FIGS. 2 and 3, the clot retrieval system includes a push wire 20a having a distal end 20c and a proximal area 20d with at least one expandable wire frame A, B fixed to the push wire 20a adjacent the distal end 20c. As shown, the CRS may include more than one wire frames (A and B) or possibly more; however, generally no more than 3 or 4. More than one wire frame may increase the likelihood that a clot may be recovered. Each wire frame may be collapsed within a MC to convey the CRS to the occlusion site as shown in FIG. 4 where upon deployment, each wire frame will expand to an expanded shape as determined by its wire memory and the actions of the operator. Generally, as shown in FIGS. 2 and 3, the approximate overall length between the proximal end 20d and distal end 20c will be in the range of 20 mm when expanded and 30 mm when compressed for a CRS having two wire frames.

As shown in FIGS. 2 and 3, the distal most wire frame A has a distal end 20c fixed to the push wire 20a. The proximal end 20d(A) of wire frame A is slidingly engaged with the push wire in a manner such that as the push wire is pulled proximally, the proximal end 20d(A) will slide over the push wire and shorten the distance between the proximal end 20d(A) and the distal end 20c thus allowing the wire frame A to expand. As shown, the wire frame A includes an expansion stop 20g(A) that prevents distal movement of the end 20d(A) past a defined position and thus define a maximum degree of expansion of wire frame A. Similarly, wire frame B has an expansion stop 20g(B) which similarly defines a point of maximum expansion of wire frame B. Thus, in this example, wire frame A has a fixed end 20c and a free-floating end 20d(A) whilst wire frame B has two free-floating ends relative (20d(B) and 20c(B)) to the push wire 20a. For wire frames of equal size, the distance between expansion stops 20g(B) and 20g(A) and 20g(A) and end 20c will typically be equivalent.

Accordingly, during deployment of the CRS from an MC, as each wire frame emerges from the MC, it will expand to a pre-determined size based on its shape memory and generally to a size where the individual wires of the frame are in gentle contact with vessel 24. As the surgeon begins to withdraw the CRS, friction of the wire frame against the vessel may cause the wire frame to continue to expand as the distal end of the push wire is pulled proximally. As the wires are fine and depending on the friction of the wires against the vessel and/or other forces, the free-floating ends of each cage will move distally relative to end 20c until contact of the respective ends of each wire cage contact the respective expansion stops. Thus, a point of maximum extension will be defined.

Figure 5:
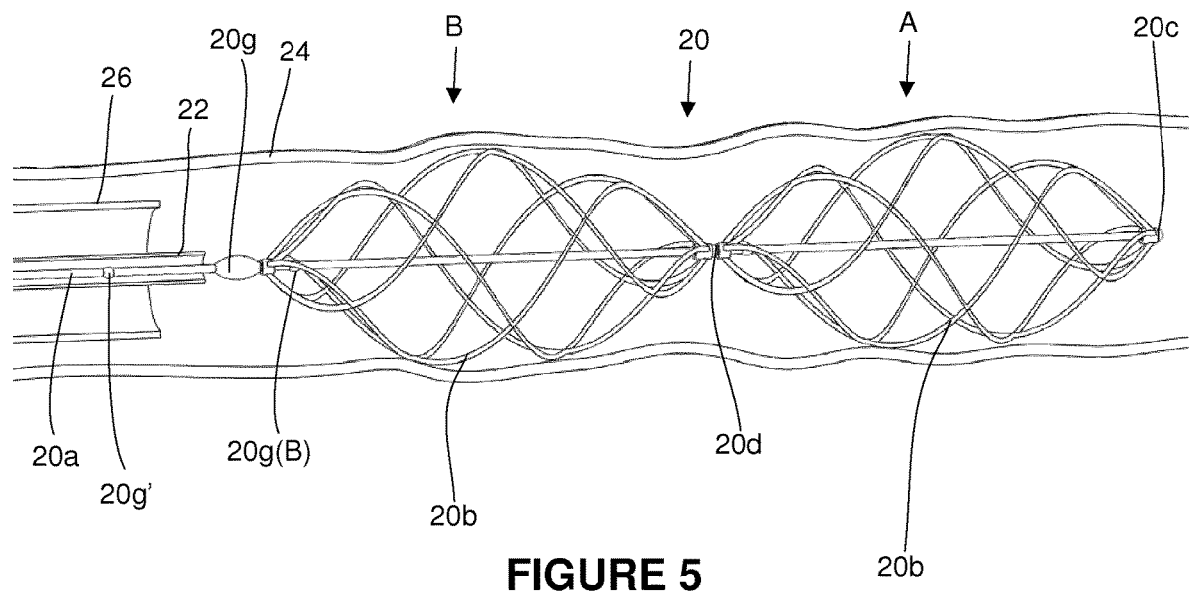
FIG. 5 is a side view of a stent system having helical wires in accordance with one embodiment of the invention

In one embodiment, in the event that the CRS includes at least a second wire frame B, as described above, the distal end of each wire frame may be fixed to the push wire with respect to the push wire. If the distal end of each wire frame is fixed to the push wire, the spacing between wire frames A and B will be determined by the collapsed length of wire frame A as shown in FIG. 5. However, in this case, there will be a short gap between each wire frame when the wire frames are fully expanded. In other words, different embodiments may have wire frames having various combinations of fixed and free-floating ends where the spacing between wire frames is determined by the position of different expansion stops.

In one embodiment, in order to assist in the expansion of the wire frames and in the case where the wire frame B is free-floating with respect to the push wire, the push wire is provided with a proximal plug 20g that forms a proximal anchor point that resists proximal movement of the push wire. The proximal plug 20g is free-floating with respect to the push wire 20a. In this case, as the push wire is being pulled proximally, the proximal plug can slide along the push wire 20a and will engage with the distal edge 22a of the MC such that the proximal plug 20g engages with the proximal end of wire frame B thus causing the proximal end to move towards the distal end of wire frame B thus causing wire frame B to expand. Importantly, as the proximal plug 20g is pushed out of the MC during deployment it must be able to remain stationary with respect to the push wire during deployment. As such, the proximal plug is prevented from sliding proximally along the push wire by a lock point 20g' as shown in FIGS. 2-5.

The proximal plug in this case is sized and shaped so as to expand slightly as it emerges from the MC such that during proximal movement of the push wire after deployment, the outer surfaces of the proximal plug will engage with the distal edge of the MC and thus slide over the push wire and engage with the proximal end of wire frame B. Generally, the tolerances of the proximal plug 20g must be such that the CRS can be deployed from the MC whilst providing some resistance to proximal movement of the push wire so as to promote wire frame expansion. As is understood by those skilled in the art, the pressures during deployment and clot retrieval are subtle.

As shown in FIG. 4, prior to deployment, each wire frame A B and microcatheter (MC) stop 20g (if present) are compressed and fully retained within microcatheter 22. Generally, after the surgeon has positioned the guide catheter 26, MC 22 and compressed CRS at the desired site, the surgeon gently holds the push wire in position and withdraws the MC such that the CRS emerges from the MC 22 and expands into the vessel 24 as shown in FIGS. 2 and 3. In order to prevent, the proximal plug 20g from sliding in a proximal direction as the MC is being drawn proximally, the push wire is provided with a push wire stop 20g' that prevents this movement.

Figure 6:
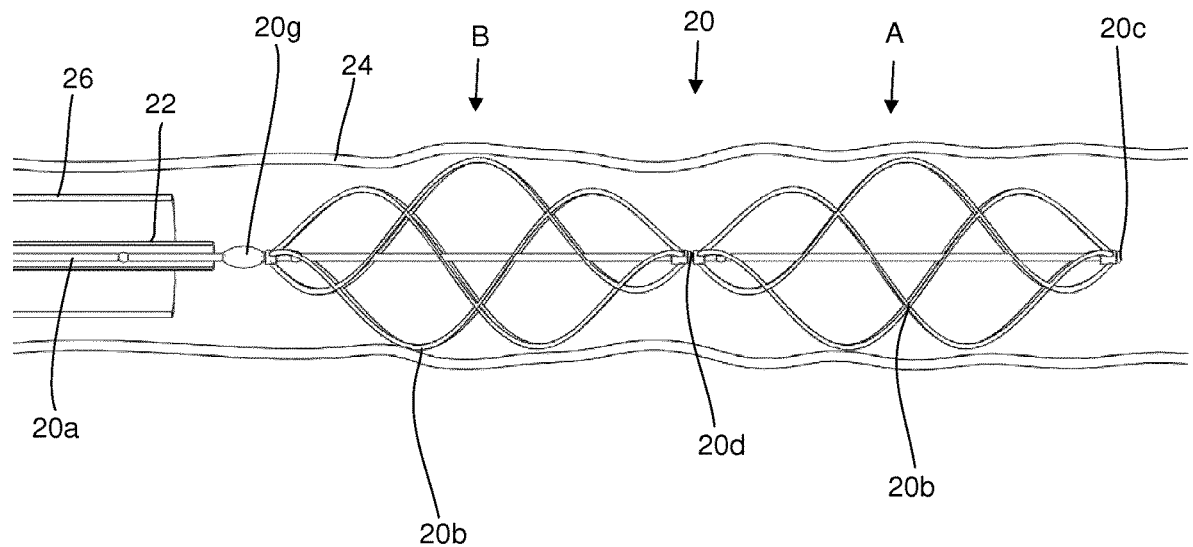
FIG. 6 is a perspective view of a stent system having helical wires in accordance with one embodiment of the invention.

In the embodiment as shown in FIG. 2, the wire frame 20b of wire frame A is illustrated as having 6 individual wires (20b1-6) that are outwardly curved between the distal and proximal ends of each wire frame. FIG. 3 shows wire frames having 4 wires. Generally, each wire frame will have at least three wires to ensure the wire frames are centralized within the vessel and more preferably will be 4-6 wires. The wire frames can be in may different shapes and configurations. They may have a continuous wire frame (closed cell design as shown in FIGS. 5 and 6) or discontinuous wire frame (open-cell design as shown in FIGS. 2 and 3).

Various functional features and operation of the CRS are described in relation to individual components of the CRS.

Wire Frame

The wire frames (A, B) are primarily intended to provide surfaces to which a clot may adhere and otherwise become entangled. In various embodiments, each wire frame will have various combinations of the following structures and functions:

Materials: The wire frame is fabricated from suitable metals as utilized in prior art stents. In particular, shape memory alloy wires are particularly effective in stent applications such as Nitinol alloys.

Size and Shape: Each wire frame when expanded will have a typical length of approximately 5-40 mm. As noted above, a number of wire frames may be configured to a push wire such that the overall length of the stent is approximately 20-40 mm. The expanded diameter of the wire frame will typically correspond to the diameter of the occlusion site which is typically in the range of 3-6 mm. As shown in the Figures, the wire frame has a generally convex surface. In a longer wire-frame the central part of the wire frame may be cylindrical to allow better apposition against the wall of the vessel. However, other shapes may be implemented (see FIGS. 5 and 6).

Expansion Stop

The expansion stops are positioned to define the maximum extension of each wire frame and thereby control its shape during the process of withdrawing a clot. This prevents further opening of the wire frame and minimizes the risk of distortion of the wire frame which can be particularly advantageous when withdrawing a clot a region of high tortuosity. In addition, the ability of the surgeon to selectively apply pressures to both the push wire and MC during clot removal can enable the surgeon to control the stiffness of the CRS during a procedure. After the stent is deployed, as the surgeon pulls the wire relative to the microcatheter, proximal plug 20g comes against the tip of the microcatheter and provides counter resistance. As a consequence 20g(B) comes closer to 20g thus shortening the total length from 20g to 20c. This ability can enable the surgeon to prevent or minimize the collapse of a stent which can improve the ability to retain a clot and prevent its release after capture.

In various embodiments, the expansion stop will have various combinations of the following structures and functions:

Position: Typically, each expansion stop will be positioned to limit the curvature of the wire frame to an outer shape as the axial length of the wire frame shortens (i.e. the length between the proximal and distal ends of each wire frame) and the radial length lengthens (ie. the perpendicular distance between the push wire and point of maximum extension of the frame). That is, preferably the radial length R remains less than or equal to the axial Length A such that the diameter of the wire frame is less than the length of the wire frame.

Materials: The expansion stop may be fabricated from any suitable metal or plastic.

Proximal Plug

Figure 7A:
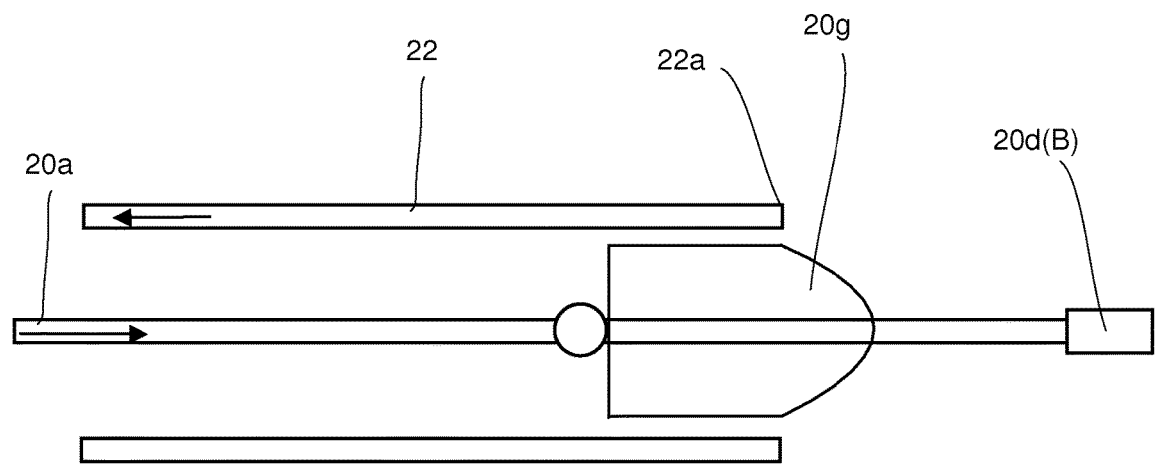
FIGS. 7A and 7B are schematic sketches showing how a proximal plug may provide resistance to enable expansion of a wire frame after deployment of a stent from a microcatheter.
Figure 7B:
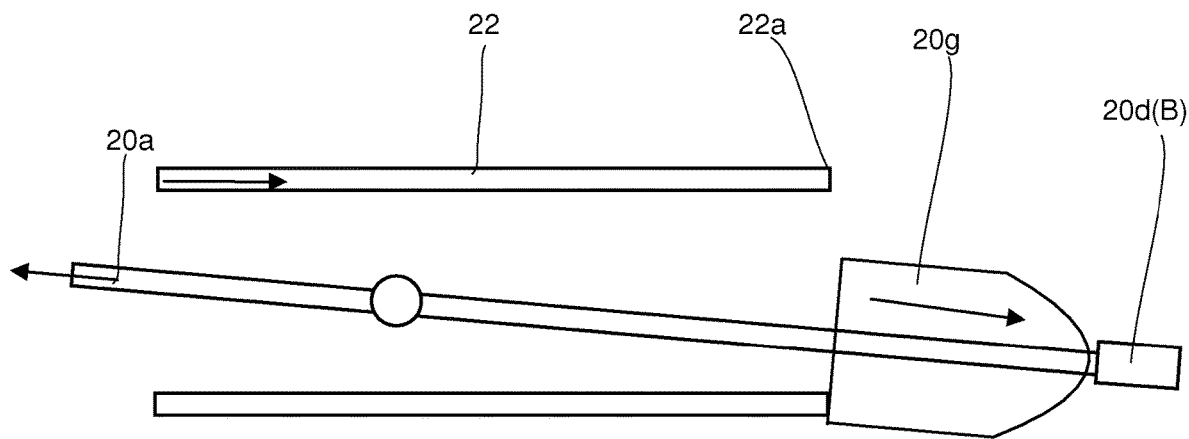

The proximal plug (PP) 20g is primarily intended to provide resistance to the movement of the push wire as the push wire is moved proximally with respect to the microcatheter. In one embodiment, the PP is a resiliently flexible stop (e.g. a small elliptical or bullet shaped bead or an expandable disk) telescopically engaged over the push wire. When deployed, namely when the stent has been extended from the microcatheter, the PP may become misaligned with respect to the distal end of the MC such that subsequent contact of the PP with the MC will result in resistance thus causing extension of the wire frames as the guide wire and MC are manipulated. In other words, the shape and size and geometry of the PP is such that it allows smooth forward and backward movement while it is within the MC. However once outside it provides resistance to returning inside the microcatheter again as it will not be centered. FIGS. 7A and 7B show how a PP may move freely within a MC prior to and during deployment but may resist re-entry into the MC after deployment due to misalignment.

Depending on the particular geometries of a wire frame, the proximal plug will prevent the wire frame from withdrawing into the MC during gentle proximal movement of the push wire. However, the proximal plug will preferably have a threshold pressure (or a pressure release procedure) that once overcome (or released) will allow the proximal plug to collapse and be drawn into the MC in which case the wire cages may collapse and also be withdrawn into the MC. In various embodiments, the expansion stop will have various combinations of the following structures and functions:

Materials: The proximal plug is fabricated from suitable metals or plastics having sufficient resilience and flexibility to permit distal movement of the CRS through the MC, expansion to a size larger than the MC (or can be prevented from re-entering the MC through pressure control techniques) and to resist proximal movement of a wire frame into the MC.

Shape and Size: The proximal plug may have a variety of expanding shapes and sizes to provide the above described functions.

Other Embodiments

FIGS. 5 and 6 show an alternate embodiment of the wire frame in accordance with one embodiment of the invention. In this embodiment, each wire frame A, B includes 2 or more helical wires 20b extending between the distal end 20c of the wire frame to its proximal end 20d. In this embodiment, the helical wires criss-cross with respect to one another so as to form an outer cage structure. Similar mechanisms to control the expansion of the wire frames as described are also provided.

Other Features

Preferably, the CRS will include markers on the proximal ends of the MC and guide/push wires 20a to provide the surgeon information with respect to the relative position of the MC and guide wire with respect to one another during a procedure. In particular, the relative position of markers on the push wire relative to the proximal end of the microcatheter will provide the surgeon with feedback regarding the degree of expansion of the wire cage and thus provide an indication of how stiff the expanded wire frames may be at a particular moment. That is, if the distance between different markers is greater as the surgeon is applying a separating force to the MC and CRS, this may be used to signal that the wire frames are maximally extended and thus stiffer. By shortening the distance, the wire frames can be made more pliable.

Typical Dimensions

For the purposes of illustration, Table 2 shows approximate dimensions of various components of the system.

TABLE 2

| Typical Dimensions | |
|---|---|
| Component | Range (mm) |
| Typical Vessel Diameter with Clot | 3-5 mm |
| Guide Catheter OD | 2.5-3.5 |
| Microcatheter OD | 0.5-0.7 |
| Push Wire OD | 0.2-0.3 |

TABLE 2-continued

| Typical Dimensions | |
|---|---|
| Component | Range (mm) |
| Wire of Wire Frame Diameter | 0.2-0.3 |
| Wire Frame Length (per wire frame) | 5-10 |

Methods of Use

A surgeon may implement a number of different techniques to place and withdraw a CRS. As noted above, a CRS is typically deployed through a MC and withdrawn into a guide catheter. However, in various designs, the CRS may be fully withdrawn back into the MC. The surgeon will utilize a number of different push, pull and twisting techniques to properly place, deploy and withdraw a CRS during a procedure. As described above, gentle extension and retraction techniques of the MC relative to the push wire can be used to control the stiffness of the wire frames.

Although the present invention has been described and illustrated with respect to preferred embodiments and preferred uses thereof, it is not to be so limited since modifications and changes can be made therein which are within the full, intended scope of the invention as understood by those skilled in the art.

The invention claimed is:

1. A blood clot retrieving apparatus for deployment into a patient's vasculature from a microcatheter and for retrieving an intravascular blood clot from within the patient's vasculature comprising:
   a push wire;
   an expandable wire frame having a wire frame distal end fixed to the push wire adjacent a distal end of the push wire and a wire frame proximal end slidingly engaged with the push wire, the expandable wire frame having a plurality of expandable wires extending between the wire frame distal end and wire frame proximal end, the expandable wire frame expandable from a compressed position within the catheter to an uncompressed deployed position;
   an expansion stop fixed to the push wire, the expansion stop positioned on the push wire between the wire frame distal end and wire frame proximal end to define a minimum distance between the wire frame distal end and wire frame proximal end of the expandable wire frame and a point of maximum extension of the expandable wire frame;
   a proximal microcatheter plug frictionally and slidingly engaged with the push wire proximal to the wire frame proximal end, the proximal microcatheter plug sized to enable proximal and distal movement of the proximal microcatheter plug within the microcatheter, emergence from the microcatheter, engagement with the wire frame proximal end and to resist re-engagement of the proximal microcatheter plug within the microcatheter; and
   a push wire stop proximal to the proximal microcatheter plug preventing proximal movement of the proximal microcatheter plug.

2. The apparatus as in claim 1, wherein each expandable wire defines a generally arcuate shape between the wire frame distal end and the wire frame proximal end.

3. The apparatus as in claim 1, wherein the expansion stop is an enlarged section fixed to the push wire.

4. The apparatus as in claim 1, wherein the expandable wire frame plurality of expandable wires extending between the wire frame proximal end and the wire frame distal end and wherein the at least two helical wires intersect over one another.

5. The apparatus as in claim 1, wherein the expandable wire frame is two or more expandable wire frames each operatively connected to the push wire and the wire frame distal end of each expandable wire frame is fixed to the push wire and each expandable wire frame has a corresponding expansion stop.

6. The apparatus as in claim 5, wherein each expansion of each wire frame is spaced along the push wire at a separation to enable each wire frame to be compressed within a microcatheter.

7. The apparatus of claim 1, wherein the proximal microcatheter plug has a plug distal end configured for egress from the microcatheter and a plug proximal end configured to restrict entry back into the microcatheter once ejected.

8. A blood clot retrieving apparatus for deployment into a vasculature of a patient from a microcatheter and for retrieving an intravascular blood clot from within the patient's vasculature comprising:
a push wire comprising a push wire distal end;
an expandable wire frame comprising a wire frame distal end fixed to the push wire adjacent the push wire distal end of the push wire and a wire frame proximal end slidingly engaged with the push wire, the expandable wire frame having a plurality of expandable wires extending between the wire frame distal end and wire frame proximal end, the expandable wire frame being configured to expand from a compressed position within the catheter to an uncompressed deployed position;
an expansion stop fixed to the push wire, the expansion stop being positioned on the push wire between the wire frame distal end and wire frame proximal end to define a minimum distance between the wire frame distal end and the wire frame proximal end of the expandable wire frame and a point of maximum extension of the expandable wire frame;
a proximal microcatheter plug frictionally and slidingly engaged with the push wire proximal to the wire frame proximal end, the proximal microcatheter plug being configured to enable proximal and distal movement of the proximal microcatheter plug within the microcatheter, emergence from the microcatheter, engagement with the wire frame proximal end and to resist re-engagement of the proximal microcatheter plug within the microcatheter; and
a push wire stop proximal to the proximal microcatheter plug configured to prevent proximal movement of the proximal microcatheter plug.

9. The apparatus as in claim 8, wherein each of the plurality of expandable wires has an expandable wire proximal end, the expandable wire proximal end of at least one of the plurality of expandable wires being located between the expansion stop and the proximal microcatheter plug.

10. The apparatus as in claim 8, wherein the proximal microcatheter plug is located between the expansion stop and the push wire stop.

11. The apparatus as in claim 8, wherein each expandable wire defines a generally arcuate shape between the wire frame distal end and the wire frame proximal end.

12. The apparatus as in claim 8, wherein the expansion stop is an enlarged section fixed to the push wire.

13. The apparatus as in claim 8, wherein the plurality of expandable wires comprises at least two helical wires extending between the wire frame proximal end and the wire frame distal end and wherein the at least two helical wires intersect one another.

14. The apparatus as in claim 8, wherein the expandable wire frame is two or more expandable wire frames each operatively connected to the push wire and the wire frame distal end of each expandable wire frame is fixed to the push wire and each expandable wire frame has a corresponding expansion stop.

15. The apparatus as in claim 14, wherein each expansion of each wire frame is spaced along the push wire at a separation to enable each wire frame to be compressed within a microcatheter.

16. The apparatus of claim 8, wherein the proximal microcatheter plug has a plug distal end configured for egress from the microcatheter and a plug proximal end configured to restrict entry back into the microcatheter once ejected.

17. A method comprising the steps of:
providing a blood clot retrieving apparatus comprising a push wire, an expandable wire frame and a proximal microcatheter plug, wherein the expandable wire frame has a plurality of expandable wires connected between a wire frame proximal end slidingly engaged with the push wire and a wire frame distal end fixed to the push wire and the push wire has at least one expansion stop and a proximal microcatheter plug, the expandable wire frame being expandable from a compressed position within a microcatheter to an uncompressed deployed position, the at least one expansion stop being positioned on the push wire between the wire frame distal end and the wire frame proximal end to define a minimum distance between the wire frame distal end and the wire frame proximal end of the expandable wire frame and a point of maximum extension of the expandable wire frame, the proximal microcatheter plug being frictionally and slidingly engaged with the push wire proximal to the wire frame proximal end, the proximal microcatheter plug being sized to enable proximal and distal movement of the proximal microcatheter plug within the microcatheter, emergence from the microcatheter, engagement with the wire frame proximal end and to resist re-engagement of the proximal microcatheter plug within the microcatheter;
expanding the expandable wire frame operatively connected to the push wire from the microcatheter;
applying a distal force sufficient to cause the proximal microcatheter plug to emerge from the microcatheter and selectively applying a distal or proximal force to the push wire relative to the microcatheter, wherein the proximal microcatheter plug engages with the microcatheter to thereby control the stiffness of the expanded wire frame.

\* \* \* \* \*